Figure 1:
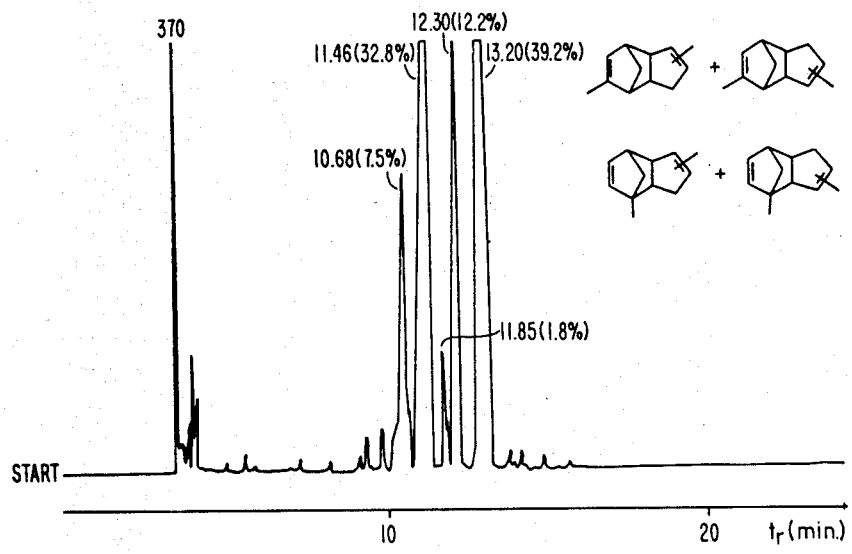

United States Patent [19]

Brunke et al.

[11] Patent Number: 4,709,061
[45] Date of Patent: Nov. 24, 1987

[54] MIXTURES OF DIMETHYL-TRICYCLO (5.2.1.02,6) DECANE DERIVATIVES TOGETHER WITH THEIR PREPARATION AND USE AS A SCENT-AND FLAVOR MATERIALS

[75] Inventors: Ernst-Joachim Brunke; Hartmut Struwe, both of Holzminden, Fed. Rep. of Germany

[73] Assignee: DRAGOCO Gerberding & Co. GmbH, Holzminden, Fed. Rep. of Germany

[21] Appl. No.: 909,514

[22] Filed: Sep. 19, 1986

Related U.S. Application Data

[63] Continuation of Ser. No. 550,947, Nov. 14, 1983, abandoned.

[30] Foreign Application Priority Data

Nov. 13, 1982 [DE] Fed. Rep. of Germany ....... 3242042

[51] Int. Cl.[4] .......................................... C07D 303/06
[52] U.S. Cl. .................... 549/544; 585/350; 585/22; 512/13
[58] Field of Search .............. 549/544; 585/350, 22; 252/522 R, 522 A

[56] References Cited

U.S. PATENT DOCUMENTS

| | | | |
|---|---|---|---|
| 3,793,348 | 2/1974 | Hochstetler et al. | 549/544 |
| 3,979,338 | 9/1976 | Sundt | 549/544 |
| 4,450,101 | 5/1984 | Spreeber et al. | 560/256 |
| 4,453,000 | 6/1984 | Shulte-Elk et al. | 560/256 |
| 4,471,135 | 9/1984 | Evers et al. | 560/256 |

FOREIGN PATENT DOCUMENTS 0187900 2/1956 Fed. Rep. of Germany ...... 549/544
1218643 6/1984 Fed. Rep. of Germany ... 252/522 R Primary Examiner—Glennon H. Hollrah
Assistant Examiner—D. L. Dinner
Attorney, Agent, or Firm—Hedman, Gibson, Costigan & Hoare

[57] ABSTRACT

Mixtures of new dimethyl-tricyclo[5.2.1.0$^{2,6}$]decane derivatives, notably the primary isomers of the common formula A, wherein
  $R^1$ and $R^2$ mean either methyl group or hydrogen, one of the substituents being a methyl group and the other hydrogen,
  $R^3$ and $R^4$ mean either methyl group or hydrogen, one of the substituents being a methyl group and the other hydrogen, and
  X indicates the π-system of a C-C double bond or an epoxide system, can advantageously be used as new acent- and flavor materials.

The compounds of the common formula A, were prepared by hydrogenation of dimeric methylcyclopentadiene selectively in the norbornane part and when desired by epoxidation of the remaining double bond.

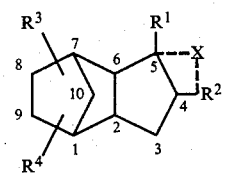

X = π-system, —O—

2 Claims, 10 Drawing Figures

MIXTURES OF DIMETHYL-TRICYCLO (5.2.1.02,6) DECANE DERIVATIVES TOGETHER WITH THEIR PREPARATION AND USE AS A SCENT-AND FLAVOR MATERIALS

This application is a continuation of application Ser. No. 550,947, filed 11/14/83, now abandoned.

Description

Dicyclopentadiene (1) is an important starting material for scent production. Ester 2b–c obtained by the addition of carboxylic acids (e.g. acetic acid, propionic acid) are used for scents worldwide in large amounts (preparation: Zeilanov et al., Chem. Abstracts 68, 49319d). The format 2a is described in U.K. Pat. No. 815,232 (24.6.1959) and the dimethylacrylate 2d in U.S. Pat. No. 3,593,745 (10.8.1971). Further products from dicyclopentadiene were comprehensively described by Ohloff and Rodé-Gawal (in: H. Aebi, E. Baumgartner, H. P Fiedler and G. Ohloff, "Kosmetika, Riechstoffe und Lebensmittelzusatzstoffe"; G. Thieme Verlag, Stuttgart 1978, pp. 55-57).

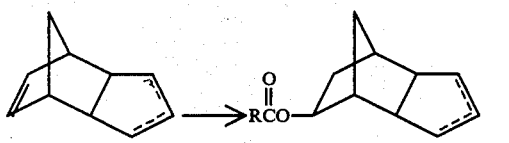

2a: R = H
2b: R = Me
2c: R = Et

2d: R = 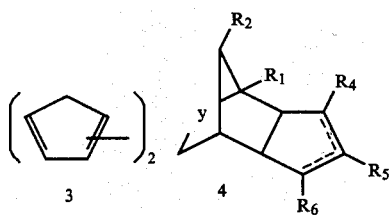

$R_1, R_2$ = H, CH$_3$/CH$_3$, H
$R_3$ = H, C$_1$-C$_3$—Acyl, C$_{3-0}$
C$_4$—Alkyl-, C$_3$— or C$_4$—Alkenyl
$R_4, R_5, R_6$ = CH$_3$, H, H/
H$_2$CH$_3$, H/H, H, CH$_3$ Little is known about the products of dimeric methylcyclopentadiene (3). In European patent application No. 0 039 232 were claimed as scents dimethyltricyclodecane derivatives of the common formula 4 obtained from dimeric methyl cyclopentadiene 3, the broken line representing an optional double bond. The methyl group in the norbornane part should alternatively be contained in the R$_1$ or R$_2$ group and the methyl group in the cyclopentene part should alternatively be contained in the R$_4$, R$_5$ or R$_6$ group. The respective non-substituted positions R$_1$, R$_2$, R$_{4-6}$ should be occupied by hydrogen. The molecular group Y should be a carbonyl—, hydroxyl—, acetate—, propionate—, or a C$_3$— or C$_4$— ether group. The products consist of isomeric mixtures.

Compounds of the common formula 5 were claimed in German patent specification No. 1 218 643 (6.6. 1966), possessing perfume properties.

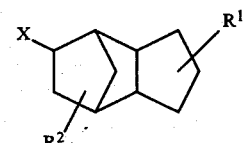

5

$R^1, R^2$: H, CH$_3$

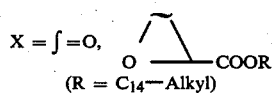

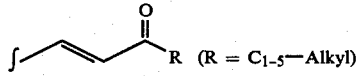

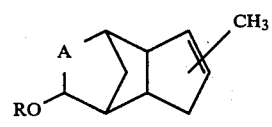

6

A = $\int$>=CH$_3$, $\int$>—CH$_3$

R = H, niedriger Acylrest

German OLS 3 120 700 A1 (25.2.1982) described tricyclodecane derivatives of the common formula 6 and their use as scents.

The present invention relates to a mixture of new dimethyltricyclo[5.2.1.0$^{2,6}$]decane derivatives, notably primary isomers of the common formula A

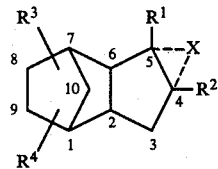

X = π-system, —O—

R$^1$ and R$^2$ mean either methyl group or hydrogen, one of the substituents being a methyl group and the other hydrogen, R$^3$ and R$^4$ mean either methyl group or hydrogen, one of the substituents being a methyl group and the other hydrogen, and X indicates the π-system of a c—c double bond or an epoxide system.

Methylcyclopentadiene [preparation: review in W. T. Ford, J. Org. Chem. 25, 3979 (1971)] exists as a mixture of three double-bonded isomers 3a,b,c. According to S. McLean and P. Haynes, (Tetrahedron, 21, 2313 (1965)) it exists in equilibrium as 44.5% of 1-methyl-isomer 3a, 54.5% of C-2-isomer 3b and only about 1% of C-5-isomer 3c.

By the dimerisation of an equilibrium mixture of methylcyclopentadiene a plurality of products can theoretically be prepared. Under the hypothesis, that products with angular methyl groups are sterially unfavourable and do not arise in significant amounts, and that the product derived from 3c (<1%) can be ignored, the dimeric methylcyclopentadiene 3a
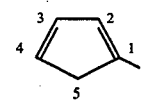
(44.5%)

3b
(54.5%)

3c
(<1%)

7a
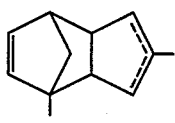
(3a + 3a)

7b
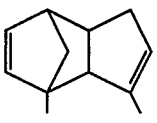
(3a + 3b)

7c
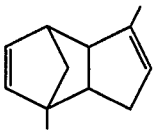

7d
(3b + 3a)

7e
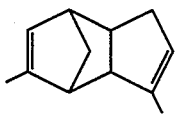
(3b + 3b)

7f
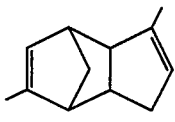

Figure 2:
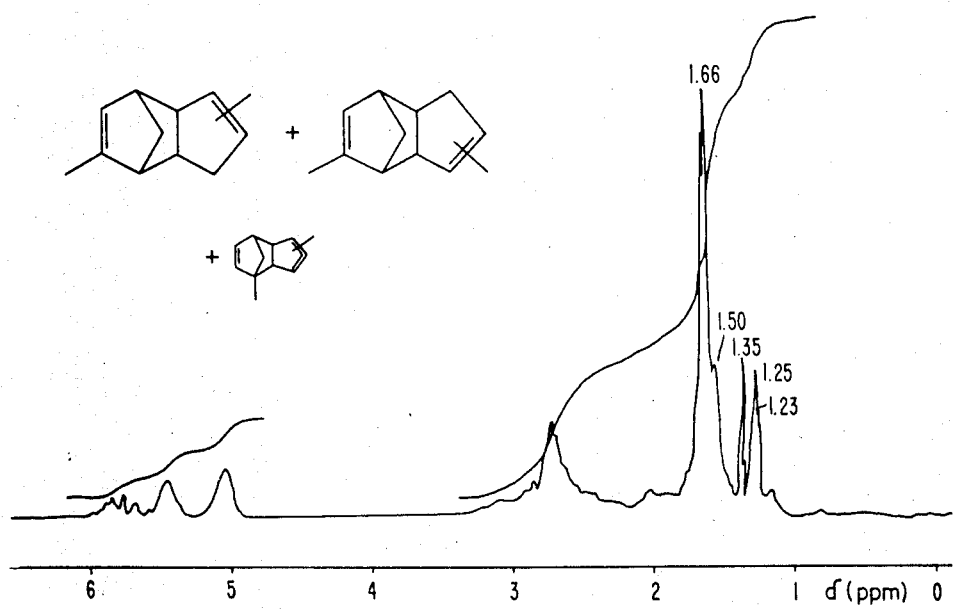

(gas chromatogram: FIG. 1) should consist of the structural isomers 7a–f. The ¹H-NMR spectrum (FIG. 2) indicates signal groups in the range of olefinic protons (5–6 ppm) which correspond to their integral 2,2 protons. The signals at 1.25 and 1.50 ppm can by analogy with dicyclopentadiene (Sadtler NMR Spectra Collection No. 6494M) be classified as the protons of the $C_1$-bridge. Only the relatively low-intensity signals of 1.23 and 1.35 ppm can be classified as the bridging methyl group of 7a–c. These findings and the intensities of the olefinic signals point to the preponderant presence of isomer 7d–f (about 85%), while 7a–c exists as only about 15%.

7a
↓ H₂/NiB

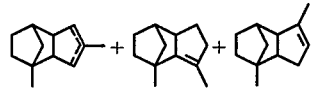
8a    8b    8c

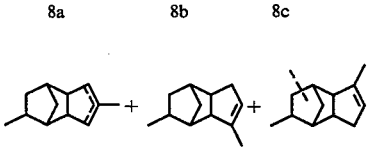
8d    8e    8f
    III

8a–f

Figure 7:
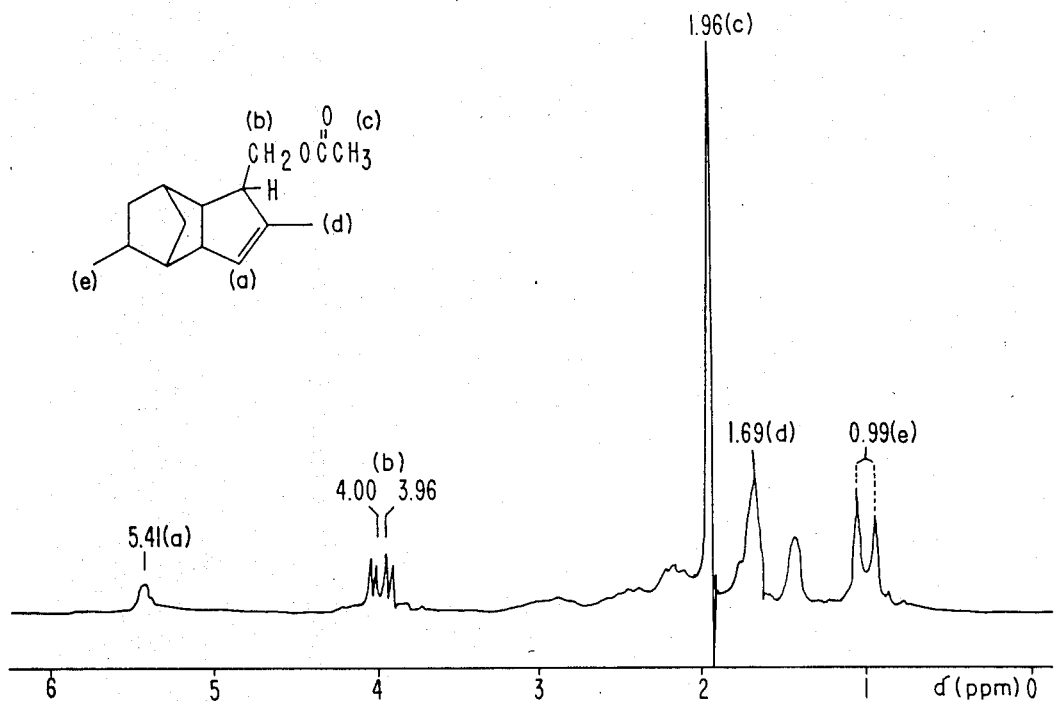

The selective hydrogenation of the norbornane part of the dimethylcyclopentadiene isomers 7a–f is achieved by modification of that of Ch. A. Brown for the selective hydrogenation of dicyclopentadiene (1) given in the review [Ch. A. Brown, Chem. Commun. 1969, 952; H. C. Brown and Ch. A. Brown, J. Am. Chem. Soc., 85, 1004 (1963)]. Using nickel boride producted in situ hydrogenation was done in methanol, ethanol, or another polar, aprotic solvent at temperatures of 20°–80° C., preferably at 40°–50° C., and a hydrogen pressure of 30–70 bar, preferably 50–60 bar. The thus-obtained new mono-enes 8a–f exist according to the gas chromatagram (FIG. 3) as a mixture of the three primary isomers (approx. 16, 24 and 37%) together with secondary isomers, that as 7a–f can be treated as structural isomers but also as stereo isomers. All these isomers show a very similar mass spectrometric breakdown pattern which can be explained by the opening of the norbornane system by formation of methylcyclopentadienyl radicals cation (m/z 80) and a methylcyclopentane (typical mass spectrum: FIG. 7). In the ¹H-NMR spectrum (FIG. 4) are the characteristic signals for olefinic protons of $\delta = 5.1–5.3$ ppm (1 H) and those for olefinic methyl groups of 1.7 ppm of the cyclopentene system with tri-substituted double bond. Singlets at 1.25 and 1.15 ppm can identify bridging methyl groups of the isomers 8a–c and two superposed doublets at 1.05 ppm the methyl groups of the norbornane part of the isomers 8d–f, that exist as primary isomers.

The mixture of mono-enes 8a–f obtained by hydrogenation of 7a–f possess a strong smell of fresh-green, herblike

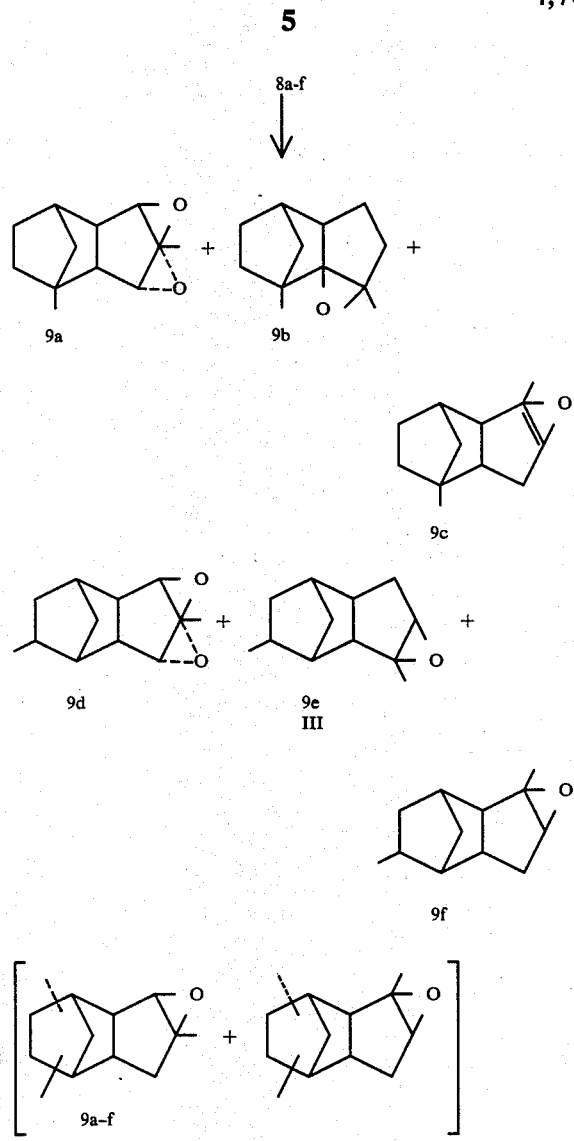

character. A solution of the mono-enes 8a-f in sugar syrup (10%) at a concentration of about 2 g/100 kg had an interesting taste tending towards aniseed and eucalyptus.

Figure 8:
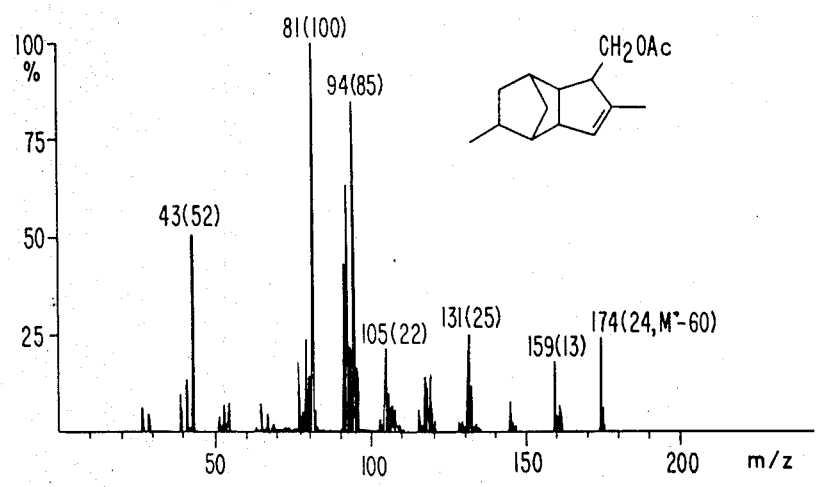
Figure 9:
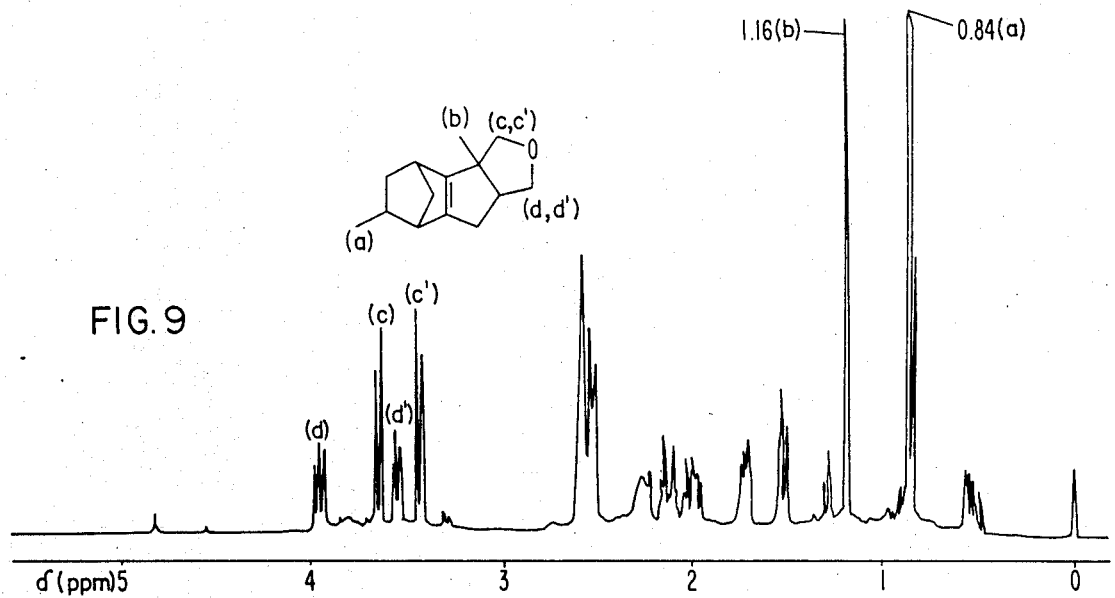
Figure 10:
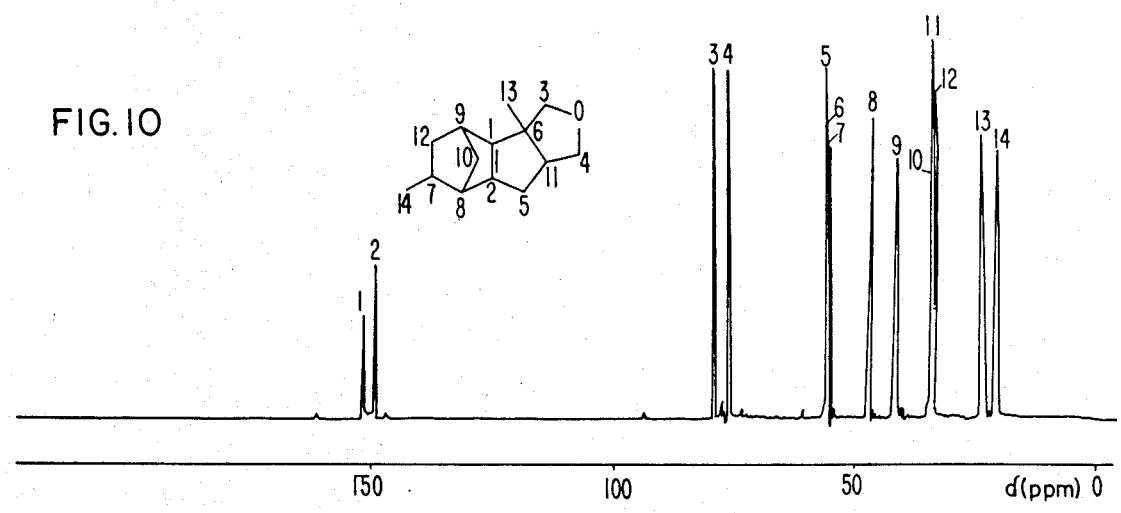

A mixture of new epoxides 9a-f was obtained by epoxidation of 8a-f. The epoxidation was carried out in known per ser manner with peracetic acid, whereby a polar, inert solvent, preferably methylene chloride or chloroform was added together with a neutralizing material, preferably sodium acetate or sodium carbonate. The mixture of new epoxides 9a-f obtained from 8a-f consists according to the gas chromatagram (FIG. 5) of three primary components (a: 15%, b: 44%, c: 32%) and a few secondary components. The three primary components show distinct mass spectrometric fragmentation behaviour (FIGS. 8, 9, 10). In the $^1$H-NMR-spectrum (FIG. 6) the abovementioned epoxide system was characterised by the signals for the oxirane proton at δ=3.0-3.2 ppm and the singlet of the methyl group at δ=1.40 ppm. The remaining methyl group signals appear analogous to 8a-f. The primary isomers should therefore possess the structures 9d-f.

The epoxide mixture 9a-f possesses a strong, fresh-herblike smell that is reminiscent of cedarleaf oil and clary sage oil. The taste of a solution of 9a-f in 10% sugar syrup at a concentration of 1 g/100 kg would be described as woody-earthy and sweet.

Because of their smell- and taste-properties the new dimethyltricyclodecane derivatives 8a-f, 9a-f (common formula A) can be used as scent- and flavour materials. This will be demonstrated by the following use examples.

EXAMPLE 1

Figure 3:
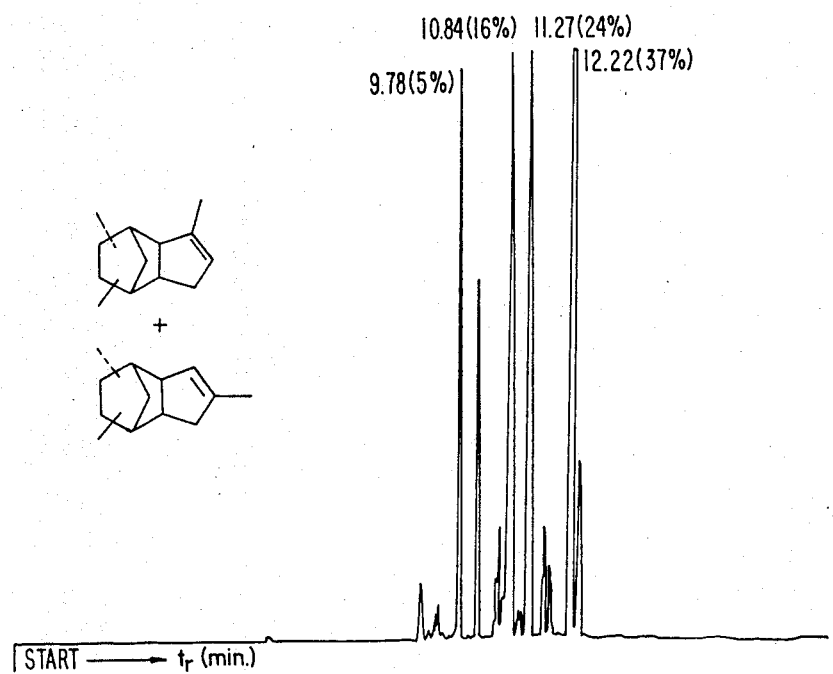
Figure 4:
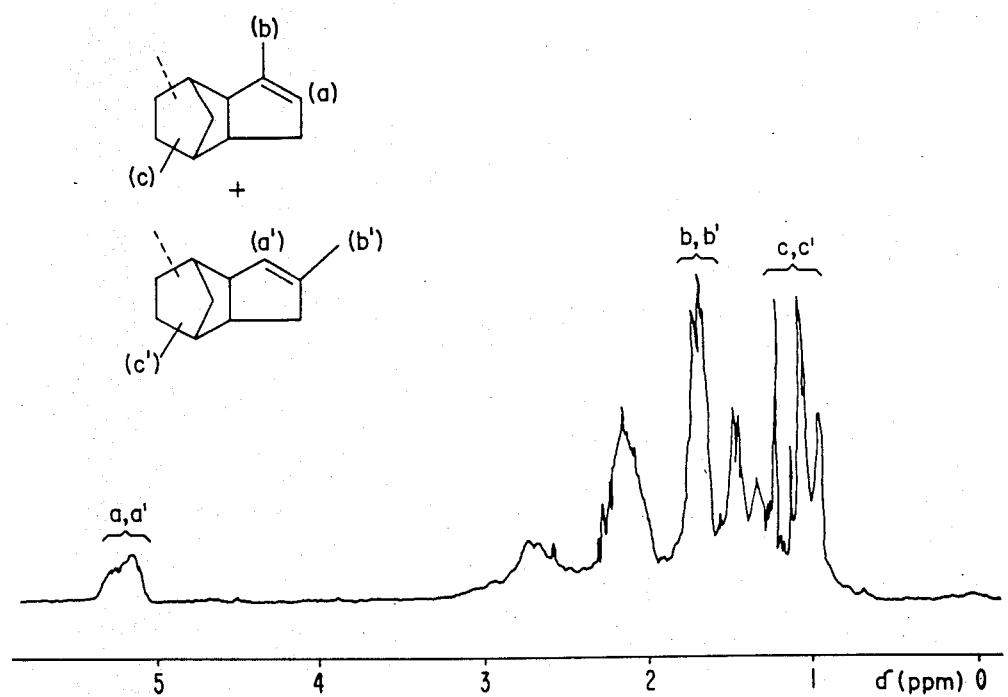

Preparation of dimethyl-tricyclo[5.2.1.0$^{2,6}$]decenes 8a-f 150 ml of an ethanolic 1 m NaBH$_4$— solution were dropped while stirring into a mixture of 139.5 g (0.56 mol). Ni(Ac)$_2$.4H$_2$O and 1.9 l ethanol in an atmosphere of nitrogen (15 min). This precipitated nickel boride as a fine-grained, black deposit. After addition of 1.44 kg (9 mol) of dimeric methylcyclopentadiene the nitrogen atmosphere was evacuated. Hydrogenation followed for 16 hours at a pressure of 50-60 bar and a temperature of 40°-50° C. After filtration, concentration and distillation 2.57 kg (88%) 8a-f was obtained as a colourless oil; bp (2.67 mbar)=76°-82° C.; density d=0.9417; refraction: n=1.4989. Gas chromatogram: FIG. 3, $^1$H-NMR: FIG. 4, MS: FIG. 7. C$_{12}$H$_{18}$ (162.4).

EXAMPLE 2

Preparation of dimethyl-tricyclo[5.2.1.0$^{2,6}$]decane-epoxide 9a-f

Figure 5:
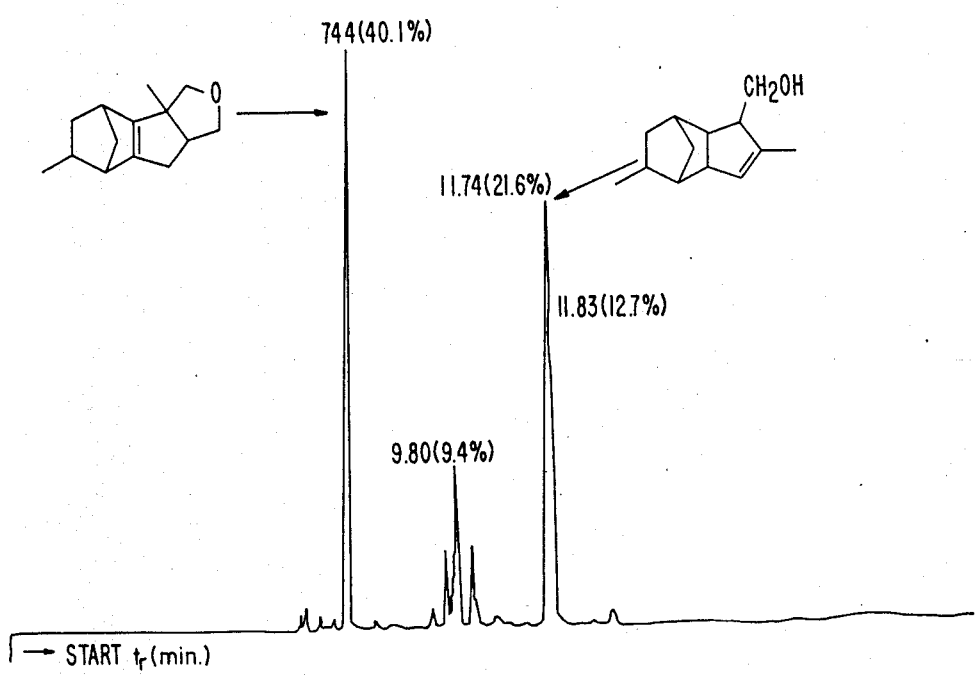
Figure 6:
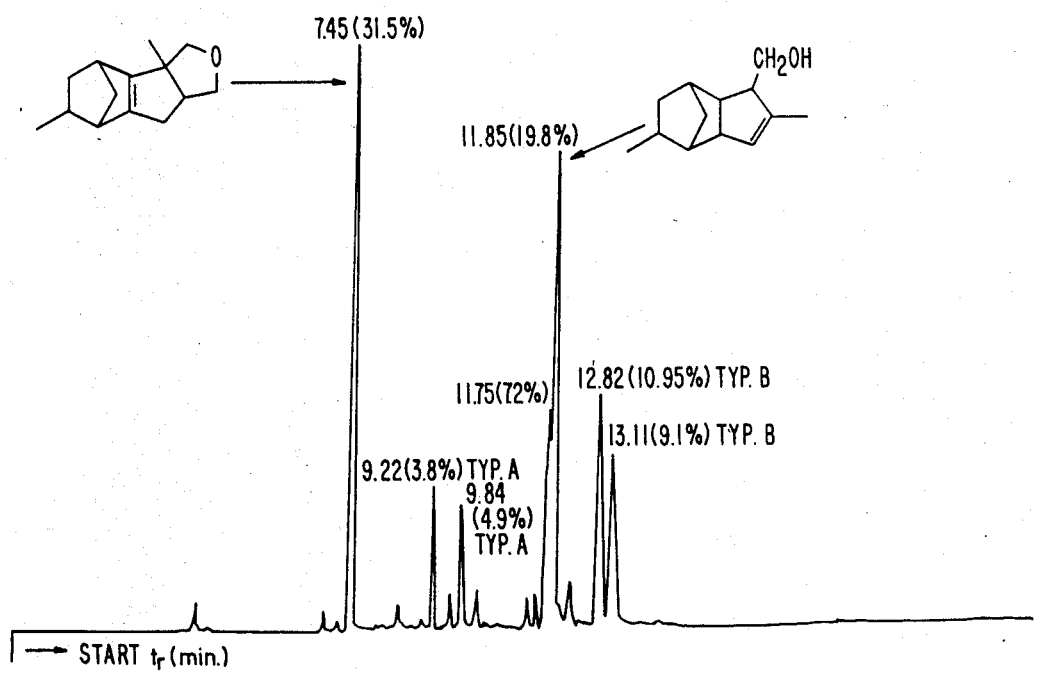

A washing of 1060 g Na$_2$CO$_3$ in 970 g (6 mol) 8a-f (according to Example 1) and 3 l CHCl$_3$ was added with 1.9 kg peracetic acid (40% in acetic acid) at 40° C. (slight cooling) for 2.5 hours. After stirring for 10 hours at room temperature 100 ml of water were added. Concentration and distillation over a 30 cm Vigreux column gave 970 g (90%) of 9a-f as a colourless oil; bp (1.35 mbar)=85°-100° C.;

density: d=1.0230; refraction: n=1.4944. GC: FIG. 5, $^1$H-NMR: FIG. 6, MS: FIGS. 8, 9, 10. C$_{12}$H$_{18}$O (178.5)

EXAMPLE 3

Perfume oil with herb-like character

|  | (a) | (b) |
|---|---|---|
| Cedar-leaf oil | 150 | — |
| epoxide 9a-f | — | 150 |
| oil of bergamot | 100 | 100 |
| phenylethyl alcohol | 100 | 100 |
| terpinol | 100 | 100 |
| acetylcedrene | 100 | 100 |
| amyl salicylate | 70 | 70 |
| linalyl acetate | 60 | 60 |
| benzyl salicylate | 50 | 50 |
| cumarine | 50 | 50 |
| 4-tert-butylcyclohexylacetate | 50 | 50 |
| anisaldehyde | 50 | 50 |
| gamma methylionone | 50 | 50 |
| linanool | 50 | 50 |
| Tunisian oil of rosemary | 45 | 45 |
| Brahmanol ® (2,2,3-trimethylcyclopent-3-ene-3'-methyl-4'-hydroxy-butyl-) | 40 | 40 |
| oil of citronella | 30 | 30 |
| ylang-ylang oil | 30 | 30 |
| attractolide (ethylenedioxo-dodecandioate) | 30 | 30 |
| oil of spike (lavender) | 20 | 20 |
| clary sage oil | 10 | 10 |
| geranium oil | 5 | 5 |
| Brasillian oil of peppermint | 5 | 5 |
| galbanum extract | 5 | 5 |
|  | 1200 | 1200 |

The perfume oil of mixture a possesses a herblike-fresh fragrance. By the exchange of the epoxide 9a–f for the cedarleaf oil a new sweet-herblike fragrance is obtained, which distinguishes itself by strong emission and cohesiveness.

EXAMPLE 4

Perfume base with green character

|  | (a) | (b) |
|---|---|---|
| benzyl salicylate | 200 | 200 |
| α-hexyl-cinnamaldehyde | 200 | 200 |
| linalylacetate | 200 | 200 |
| methyldihydrojasmonate | 100 | 100 |
| oil of basil | 80 | 80 |
| storax extract | 20 | 20 |
| oil of wormwood | 10 | 10 |
| citral | 10 | 10 |
| dimethytricyclodecene 8a–f | — | 70 |
| dipropylene glycol | 170 | 110 |
|  | 1000 | 1000 |

The perfume base of mixture a has a measurable green-fruity fragrance. The addition of the mono-ene 8a–f (mixture b) adds a fresh head character and a sweet-herblike secondary character, so that mixture b has a natural effect.

EXAMPLE 5

Perfume oil-base of "chrysanthemum-green" type

| epoxide 9a–f | 100 |
|---|---|
| linanool | 70 |
| isoeugenol-methylether | 50 |
| campholene aldehyde | 50 |
| mandarin oil | 50 |
| oil of buchu, 1% in diproylene glycol | 50 |
| Paraguayan oil of petitgrain | 40 |
| β-ionone | 30 |
| oil of basil | 20 |
| helional | 20 |
| allyl-phenoxyacetate | 10 |
| indole, 10% in diproylene glycol | 10 |
|  | 500 |

The perfume oil, which contains a large amount of 9a–f, possesses a measurable sharp-green fragrance which is reminiscent of chrysanthemum leaves.

What is claimed is:

1. Mixtures of dimethyl-tricyclo[5.2.1.0$^{2,6}$]decane derivatives which comprise isomers of the formula

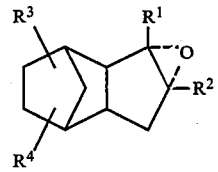

wherein $R^1$ and $R^2$ are either methyl or hydrogen with the proviso that $R^1$ and $R^2$ must be different; $R^3$ and $R^4$ are either methyl or hydrogen with the proviso that they must be different.

2. A perfumed composition which consists of an odor imparting quantity of a compound of claim 1.

* * * * *

UNITED STATES PATENT AND TRADEMARK OFFICE
CERTIFICATE OF CORRECTION

PATENT NO. : 4,709,061
DATED : November 24, 1987
INVENTOR(S) : Brunke et al.

It is certified that error appears in the above—identified patent and that said Letters Patent is hereby corrected as shown below:  Item [57]

in the Abstract, the structural formula should appear as:

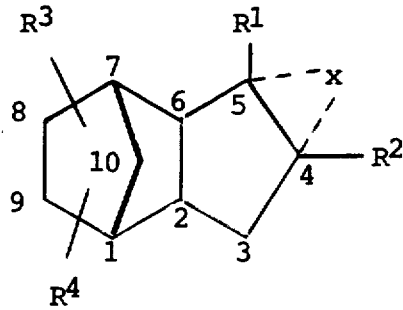

Col. 5, line 15, the structural formula should appear as:

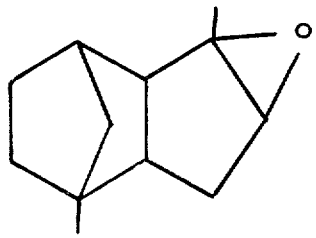

UNITED STATES PATENT AND TRADEMARK OFFICE
CERTIFICATE OF CORRECTION

PATENT NO. : 4,709,061

DATED : November 24, 1987

INVENTOR(S) : Brunke et al.

It is certified that error appears in the above-identified patent and that said Letters Patent is hereby corrected as shown below:

Cancel FIGS. 5-8 and insert:

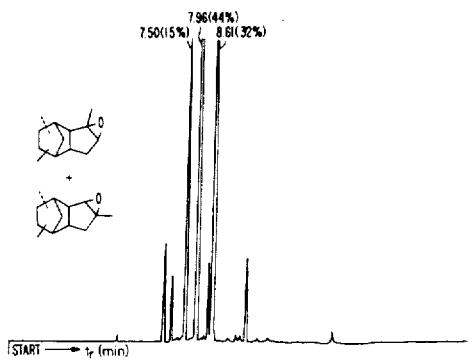

FIG. 5

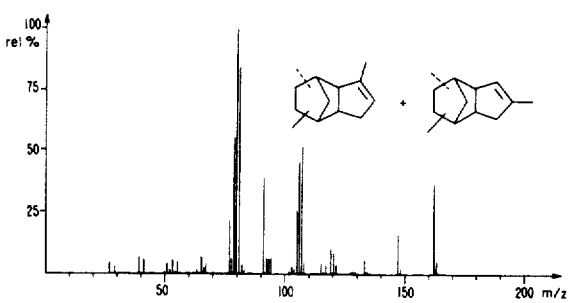

FIG. 7

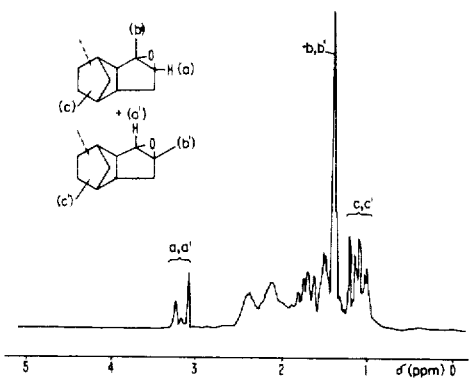

FIG. 6

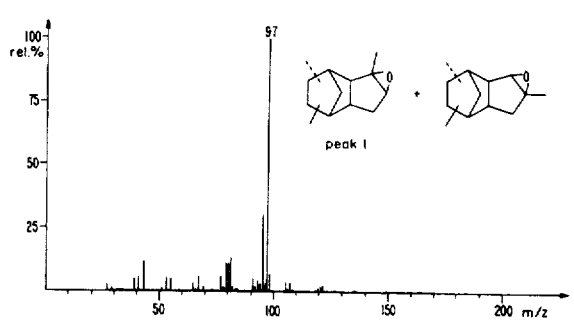

FIG. 8

UNITED STATES PATENT AND TRADEMARK OFFICE
CERTIFICATE OF CORRECTION

PATENT NO. : 4,709,061
DATED : November 24, 1987
INVENTOR(S) : Brunke et al.

It is certified that error appears in the above-identified patent and that said Letters Patent is hereby corrected as shown below:

Cancel FIGS. 9-10 and insert:

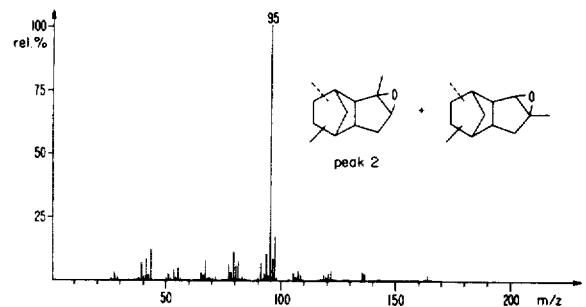

FIG. 9

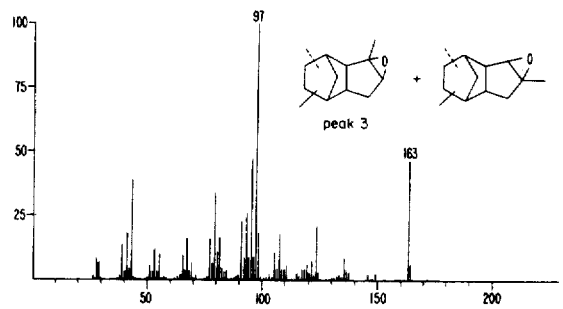

FIG. 10

Signed and Sealed this

Third Day of August, 1993

Attest:

MICHAEL K. KIRK

Attesting Officer

Acting Commissioner of Patents and Trademarks